(12) United States Patent
Gray

(10) Patent No.: US 6,486,352 B1
(45) Date of Patent: Nov. 26, 2002

(54) PROCESS FOR THE PREPARATION OF POLYALKYLPHENOXYAMINOALKANES

(75) Inventor: James A. Gray, Novato, CA (US)

(73) Assignee: Chevron Oronite Company LLC, San Ramon, CA (US)

( * ) Notice: Subject to any disclaimer, the term of this patent is extended or adjusted under 35 U.S.C. 154(b) by 0 days.

(21) Appl. No.: 10/185,469

(22) Filed: Jun. 28, 2002

(51) Int. Cl.⁷ .............................................. C07C 217/00
(52) U.S. Cl. ...................................... 564/353; 564/354
(58) Field of Search ................................ 564/353, 354

(56) References Cited

U.S. PATENT DOCUMENTS

| | | | |
|---|---|---|---|
| 4,381,401 A | 4/1983 | Poindexter | 556/410 |
| 5,669,939 A | 9/1997 | Cherpeck | 44/425 |
| 5,851,242 A | 12/1998 | Cherpeck et al. | 44/425 |
| 6,384,280 B1 | 5/2002 | Cherpeck | 564/353 |

FOREIGN PATENT DOCUMENTS

| | | |
|---|---|---|
| DE | 19711004 A1 | 10/1997 |
| JP | 2592732 B2 | 3/1997 |

OTHER PUBLICATIONS

Martin E. Dyen and Daniel Swern, *Chemistry Reviews* (1967), pp. 197–246.

*Primary Examiner*—Samuel Barts
(74) *Attorney, Agent, or Firm*—Steven G. K. Lee

(57) ABSTRACT

A process for the preparation of polyalkylphenoxyaminoalkanes which comprises the aminoethylation of a polyalkylphenol compound in the presence of a basic catalyst with β-amino alcohol or derivative thereof having the following structure:

$$R_1NH-CHR_2-CH_2-OH$$

and a dialkyl carbonate having the following formula:

$$(R_3O)_2CO$$

wherein $R_1$ and $R_2$ are independently hydrogen or lower alkyl having 1 to about 6 carbon atoms, hydroxylalkylene, phenyl, alkaryl, or aralkyl, $R_3$ is lower alkyl having 1 to about 6 carbon atoms, and wherein the polyalkyl group of said polyalkylphenol has an average molecular weight in the range of about 600 to 5,000. Optionally, an alcohol co-solvent having the structure $R_4$—OH wherein $R_4$ is an alkyl group of about 4 to 10 carbon atoms may be used.

32 Claims, No Drawings

PROCESS FOR THE PREPARATION OF POLYALKYLPHENOXYAMINOALKANES

FIELD OF THE INVENTION

The present invention relates to a process for the preparation of polyalkylphenoxyaminoalkanes. More particularly, this invention relates to a process for the preparation of polyalkylphenoxyaminoalkanes which comprises the aminoethylation of a polyalkylphenol compound with β-amino alcohol and dialkyl carbonate.

BACKGROUND OF THE INVENTION

Polyalkylphenoxyaminoalkanes are known fuel additives useful in the prevention and control of engine deposits. U.S. Pat. Nos. 5,669,939 and 5,851,242 describe a process for preparing these compounds. The process involves initially hydroxylating a polyalkylphenol with an alkylene carbonate in the presence of a catalytic amount of an alkali metal hydride or hydroxide, or alkali metal salt, to provide a polyalkylphenoxyalkanol which is subsequently reacted with an appropriate amine to provide the desired polyalkylphenoxyaminoalkane.

2-oxazolidinones or derivatives thereof are well described in the art. For example, Martin E. Dyen and Daniel Swern, *Chemistry Reviews* (1967), pages 197–246 describes 2-oxazolidinones in detail. The use of 2-oxazolidinones or derivatives thereof in the aminoethylation of phenols is well known in the art. This same reference also describes the preparation of both carbamate derivatives and 2-oxazolidinones using various β-amino alcohols and dialkyl carbonates.

U.S. Pat. No. 4,381,401 discloses the reaction of 2-oxazolidinone or N-substituted derivatives thereof with aromatic amine hydrochlorides at elevated temperatures to produce 1,2-ethanediamines. The 1,2-ethandiamines produced are an important class of materials which are useful as intermediates for the production of pharmaceuticals, photographic chemicals and other compositions.

Japanese Patent Publication No. JP 2592732 B2 discloses a method of producing phenoxyethylamines by reacting, under base conditions, low molecular weight phenols and 2-oxazolidinone. Phenoxyethylamines are important raw materials for pharmaceuticals and pesticides.

German Patent Publication DE 19711004 A1 discloses the use of 2-oxazolidinone to prepare phenoxyaminoalkanes from low molecular weight phenols. 2-4-(Phenoxyphenoxy) ethylamine and ethyl 2-(phenoxyphenoxy)ethylcarbamate are sequentially prepared in high yield and selectivity by the aminoethylation of 4-phenoxyphenol with 2-oxazolidinone under inert atomsphere, followed by amidation of 2-4-(phenoxyphenoxy)ethylamine with carbonate derivatives.

U.S. Pat. No. 6,384,280 teaches the use of 2-oxazolidinone or a derivative thereof in aminoethylation transformations involving high molecular weight polyalkylphenols to provide polyalkylphenoxyaminoalkanes of the type disclosed in U.S. Pat. Nos. 5,669,939 and 5,851,242. There has heretofore not been any teaching wherein the combination of β-amino alcohol and dialkyl carbonate or a derivative thereof has been used in aminoethylation transformations involving high molecular weight polyalkylphenols.

SUMMARY OF THE INVENTION

The present invention provides a novel process for the preparation of polyalkylphenoxyaminoalkanes which comprises the aminoethylation of a polyalkylphenol compound in the presence of a basic catalyst with a β-amino alcohol or derivative thereof having the following formula:

$$R_1NH\text{—}CHR_2\text{—}CH_2\text{—}OH$$

wherein $R_1$ and $R_2$ are independently hydrogen, lower alkyl having 1 to about 6 carbon atoms, hydroxyalkylene, phenyl, alkaryl or aralkyl;
and a dialkyl carbonate having the following formula:

$$(R_3O)_2CO$$

wherein $R_3$ is lower alkyl having 1 to about 6 carbon atoms and wherein the polyalkyl group of said polyalkylphenol has an average molecular weight in the range of about 600 to 5,000.

Optionally, the aminoethylation reaction may be carried out with an alcohol co-solvent.

The aminoethylation reaction of the present invention readily occurs using a basic catalyst selected from the group consisting of alkali metal lower alkoxides, alkali hydrides or alkali metal hydroxides in the temperature range of about 100° C. to 250° C., wherein the molar ratio of β-amino alcohol and dialkyl carbonate to polyalkylphenol compound is about 0.9–5:0.9–5:1, wherein the molar ratio of the optional alcohol co-solvent to polyalkylphenol compound, when it is used, is about 0.2:1 to 5:1 and wherein the number of equivalents of basic catalyst per equivalent of polyalkylphenol is about 0.05:1 to 1:1.

DETAILED DESCRIPTION OF THE INVENTION

Definitions

Prior to discussing the present invention in detail, the following terms will have the following meanings unless expressly stated to the contrary.

The term "alkyl" refers to both straight- and branched-chain alkyl groups.

The term "alkaryl" refers to the group:
wherein $R_a$ and $R_b$ are each independently hydrogen or an alkyl group, provided at least one of $R_a$ and $R_b$ is alkyl. Typical alkaryl groups include, for example, tolyl, xylyl, cumenyl, ethylphenyl, butylphenyl, dibutylphenyl, hexylphenyl, octylphenyl, dioctylphenyl, nonylphenyl, decylphenyl, didecylphenyl, dodecylphenyl, hexadecylphenyl, octodecylphenyl, icosphenyl, tricontylphenyl, and the like.

The term "alkylphenyl" refers to an alkaryl group of the above formula in which $R_a$ is alkyl and $R_b$ is hydrogen.

The term "aralkyl" refers to the group:

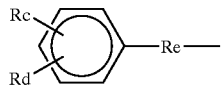

Wherein $R_c$ and $R_d$ are each independently hydrogen or a lower alkyl group, and $R_e$ is an alkylene group. Typical aralkyl groups include, for example, benzyl, methylbenzyl, ethylbenzyl, propylbenzyl, dimethylbenzyl, phenethyl, and the like.

The term "hydroxyalkylene" refers to the group:

HO—$R_f$ wherein $R_f$ is a lower alkylene group as defined below.

The term "lower alkyl" refers to alkyl groups having 1 to about 6 carbon atoms and includes primary, secondary and tertiary alkyl groups. Typical lower alkyl groups include, for example, methyl, ethyl, n-propyl, isopropyl, n-butyl, sec-butyl, t-butyl, n-pentyl, n-hexyl, cycloalkyl such as cyclopentyl, cyclohexyl and the like.

The term "lower alkylene" refers to an alkylene group having 1 to about 6 carbon atoms, such as methylene, ethylene, propylene, butylene, pentylene, and hexylene.

The term "polyalkyl" refers to an alkyl group which is generally derived from polyolefins which are polymers or copolymers of mono-olefins, particularly 1-mono-olefins, such as ethylene, propylene, butylene, and the like. Preferably, the mono-olefin employed will have about 2 to 24 carbon atoms, and more preferably, about 3 to 12 carbon atoms. More preferred mono-olefins include propylene, butylene, particularly isobutylene, 1-octene and 1-decene. Polyolefins prepared from such mono-olefins include polypropylene, polybutene, especially polyisobutene, and the polyalphaolefins produced from 1-octene and 1-decene.

As noted above, the present invention provides a novel process for the preparation of polyalkylphenoxyaminoalkanes which comprises an aminoethylation of a polyalkylphenol compound in the presence of a basic catalyst with β-amino alcohol or derivative thereof having the following structure:

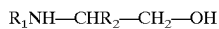
$R_1NH$—$CHR_2$—$CH_2$—OH wherein $R_1$ and $R_2$ are independently hydrogen, lower alkyl having 1 to about 6 carbon atoms, hydroxylalkylene, phenyl, alkaryl, or aralkyl;

and a dialkyl carbonate having the following formula:

$(R_3O)_2CO$ wherein $R_3$ is lower alkyl having 1 to about 6 carbon atoms; and wherein the polyalkyl group of said polyalkylphenol has an average molecular weight in the range of about 600 to 5,000.

Optionally, the aminoethylation reaction may be carried out with an alcohol co-solvent. The optional alcohol co-solvent has the structure $R_4$—OH wherein $R_4$ is an alkyl group having about 4 to 13 carbon atoms.

The reaction may be illustrated by the following:

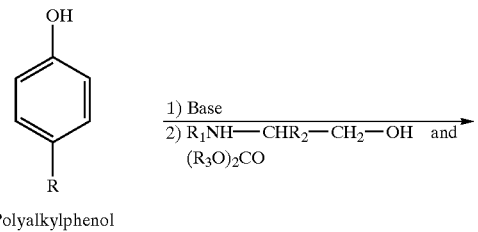

Polyalkylphenol

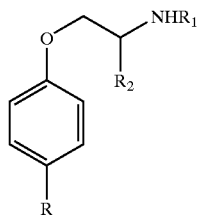

Polyalkylphenoxyaminoalkane wherein R is a polyalkyl group having a molecular weight in the range of about 600 to 5,000, and $R_1$, $R_2$ and $R_3$ are as herein described.

Polyalkylphenoxyaminoalkanes may be prepared by the process of the present invention which comprises an aminoethylation of a polyalkylphenol compound with β-amino alcohol or derivative thereof having the following formula:

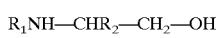
$R_1NH$—$CHR_2$—$CH_2$—OH and a dialkyl carbonate having the following formula:

$(R_3O)_2CO$ wherein $R_1$, $R_2$ and $R_3$ are defined herein, in the presence of a catalytic amount of an alkali metal lower alkoxide, alkali hydride or alkali metal hydroxide and, optionally, in the presence of an alcohol co-solvent.

Polyalkylphenols are well known materials and are typically prepared by the alkylation of phenol with the desired polyolefin or chlorinated polyolefin. A further discussion of polyalkylphenols can be found, for example, in U.S. Pat. Nos. 4,744,921 and 5,300,701.

Accordingly, polyalkylphenols may be prepared from the corresponding olefins by conventional procedures. For example, polyalkylphenols may be prepared by reacting the appropriate olefin or olefin mixture with phenol in the presence of an alkylating catalyst at a temperature of from about 25° C. to 150° C., and preferably about 30° C. to 100° C. either neat or in an essentially inert solvent at atmospheric pressure. A preferred alkylating catalyst is boron trifluoride. Molar ratios of reactants may be used. Alternatively, molar excesses of phenol can be employed, i.e., about 2 to 3 equivalents of phenol for each equivalent of olefin with unreacted phenol recycled. The latter process maximizes monoalkylphenol. Examples of inert solvents include heptane, benzene, toluene, chlorobenzene and 250 thinner which is a mixture of aromatics, paraffins and naphthenes. Other examples of inert solvents that are aromatic mixtures include Exxon Aromatic 100, Exxon Aromatic 150, Solvesso 100, Total Solvarex 9 and the like.

The polyalkyl group on the polyalkylphenols employed in the invention is generally derived from polyolefins which are polymers or copolymers of mono-olefins, particularly 1-mono-olefins, such as ethylene, propylene, butylene, and the like. Preferably, the mono-olefin employed will have about 2 to 24 carbon atoms, and more preferably, about 3 to 12 carbon atoms. More preferred mono-olefins include propylene, butylene, particularly isobutylene, 1-octene and 1-decene. Polyolefins prepared from such monoolefins include polypropylene, polybutene, especially polyisobutene, and the polyalphaolefins produced from 1-octene and 1-decene.

The preferred polyisobutenes used to prepare the presently employed polyalkylphenols are polyisobutenes which comprise at least about 20% of the more reactive methylvinylidene isomer, preferably at least about 50% and more preferably at least about 70%. Suitable polyisobutenes include those prepared using $BF_3$ catalysts. The preparation of such polyisobutenes in which the methylvinylidene isomer comprises a high percentage of the total composition is described in U.S. Pat. Nos. 4,152,499 and 4,605,808. Such polyisobutenes, known as "reactive" polyisobutenes, yield high molecular weight alcohols in which the hydroxyl group is at or near the end of the hydrocarbon chain. Examples of suitable polyisobutenes having a high alkylvinylidene content include Ultravis 30, a polyisobutene having a number average molecular weight of about 1,300 and a methylvinylidene content of about 74%, and Ultravis 10, a polyisobutene having a number average molecular weight of about 950 and a methylvinylidene content of about 76%, both available from British Petroleum.

Typically, the polyalkyl group on the polyalkylphenol has a molecular weight in the range of about 600 to 5,000, preferably about 600 to 3,000, more preferably about 700 to 3,000, and most preferably about 900 to 2,500. The polyalkyl group on the polyalkylphenol may be in any position in the phenol ring. However, substitution at the para position is preferred.

As noted above, the polyalkylphenol compound is reacted with β-amino alcohol or a derivative thereof and dialkyl carbonate having the formulas illustrated herein above, wherein $R_1$ and $R_2$ are independently hydrogen or lower alkyl having 1 to about 6 carbon atoms, hydroxyalkylene, phenyl, alkaryl or aralkyl; and $R_3$ is lower alkyl having 1 to about 6 carbon atoms. Typically, the hydroxyalkylene group will have 1 to about 6 carbon atoms, preferably 1 to about 4 carbon atoms. Preferably, $R_1$ and $R_2$ are independently hydrogen or lower alkyl. More preferably, one of $R_1$ and $R_2$ is hydrogen or lower alkyl of 1 to about 4 carbon atoms and the other is hydrogen; and $R_3$ is lower alkyl having 1 to about 4 carbon atoms. In a further preferred embodiment, one of $R_1$ and $R_2$ is hydrogen, methyl, ethyl, hydroxymethylene or hydroxyethylene, and the other is hydrogen, while $R_3$ is methyl, ethyl, propyl, isopropyl, butyl, or isobutyl. More preferably, $R_1$ is hydrogen, methyl or ethyl, $R_2$ is hydrogen or hydroxyethylene, and $R_3$ is methyl, ethyl, propyl, isopropyl, butyl, or isobutyl. Still more preferably, both $R_1$ and $R_2$ are hydrogen and $R_3$ is methyl or ethyl. Most preferably, both $R_1$ and $R_2$ are hydrogen and $R_3$ is ethyl.

Martin E. Dyen and Daniel Swern, *Chemistry Reviews* (1967), Table II, pages 201–202 describe many examples of β-amino alcohols that react with dialkyl carbonates to form carbamate intermediates and 2-oxazolidinones. In the present invention, both the carbamate intermediate and the 2-oxazolidinone are generated in situ from the β-amino alcohol and the dialkyl carbonate, and then each can independently form polyalkylphenoxyaminoalkanes by aminoethylation of a polyalkylphenol.

More specific examples β-amino alcohols include ethanolamine, diethanolamine, 2-(methylamino)-ethanol, 2-(ethylamino)-ethanol, 2-(n-propylamino)-ethanol, 2-(n-butylamino)-ethanol, 2-amino-1-propanol, 2-amino-1-butanol, 2-amino-1,3-propanediol, β-aminobenzeneethanol, 2-(phenylamino)-ethanol, and 2-(cyclohexylamino)-ethanol. Preferred are ethanolamine, diethanolamine, 2-(methylamino)-ethanol or 2-amino-1-propanol. Most preferably, the β-amino alcohol is ethanolamine.

Examples of dialkyl carbonates are dimethyl carbonate, diethyl carbonate, dipropyl carbonate, diisopropyl carbonate, dibutyl carbonate and diisobutylcarbonate. Preferred are dimethyl carbonate or diethyl carbonate. Most preferably, the dialkyl carbonate is diethyl carbonate.

Many of the β-amino alcohols and dialkyl carbonates of the present invention may be purchased from Aldrich Chemical Company or from other laboratory chemical suppliers. Alternatively, these compounds may be synthesized by conventional methods apparent to the skilled artisan.

The basic catalyst employed in the process of the present invention will generally be any of the well known basic catalyst selected from the group of alkali metal lower alkoxides, alkali hydrides or alkali metal hydroxides. Typical alkali metal lower alkoxides include, but are not limited to, sodium methoxide, potassium methoxide, sodium ethoxide, potassium ethoxide, sodium propoxide, potassium propoxide, sodium isopropoxide, potassium isopropoxide, sodium butoxide, potassium butoxide. Typically, the alkali metal lower alkoxides will contain 1 to about 6, preferably 1 to about 4, carbon atoms. Preferably, the alkali metal lower alkoxide is sodium methoxide. Sodium hydride and potassium hydride are typical alkali hydrides. Examples of alkali metal hydroxides include, but are not limited to, sodium hydroxide, lithium hydroxide, or potassium hydroxide. Sodium hydroxide and potassium hydroxide are preferred.

Typically, the reaction temperature for the aminoethylation reaction will be in the range of about 100° C. to 250° C., and preferably in the range of about 130° C. to 210° C. The reaction pressure will generally be atmospheric or lower. Lower pressures may be used to facilitate the removal of carbon dioxide. Other carbon dioxide scavengers may be employed to facilitate the reaction, such as, for example, magnesium oxide or calcium oxide.

The molar ratio of β-amino alcohol and dialkyl carbonate to the polyalkylphenol compound is normally in the range of about 0.9–5:0.9–5:1, and preferably will be in the range of about 1–2:1–2:1. In general, the number of equivalents of the basic catalyst per equivalents of polyalkylphenol will be in the range of about 0.05:1 to 1:1, and preferably in the range of about 0.1:1 to 1:1.

The aminoethylation reaction may be carried out neat or in the presence of a solvent which is inert to the reaction of the polyalkylphenol compound and the β-amino alcohol and dialkyl carbonate or a derivative thereof. When employed, a typical solvent is an aromatic solvent such as Exxon 150 aromatic solvent, although other solvents apparent to those skilled in the art may also be used. For example, any number of ethers, aprotic polar solvents or alcohols may also be useful in the process of the present invention.

The presence of an optional alcohol co-solvent is often beneficial to the aminoethylation process. The alcohol co-solvent has the structure $R_4$—OH wherein $R_4$ is an alkyl group having about 4 to 13 carbon atoms, preferably about 6 to 8 carbon atoms, most preferably about 6 carbon atoms. Examples of typical alcohols include n-butanol, 1-pentanol, 1-hexanol, 1-heptanol, 1-octanol, 1-nonanol, 1-decanol, 2-ethyhexanol, and mixed isomers of each of the foregoing alcohols including branched- or straight-chain alcohols. 1-Hexanol is preferred. Examples of commercial alcohols available from ExxonMobil Chemical that are a mix of several isomers include Exxal 6 (hexyl alcohol), Exxal 7 (isoheptyl alcohol), Exxal 10 (decyl alcohol), and Exxal 13 (tridecyl alcohol).

When an alcohol co-solvent is used, the molar ratio of the alcohol co-solvent to the polyalkylphenol compound is normally in the range of about 0.2:1 to 5:1, preferably about 0.4:1 to 2:1, and most preferably about 0.5:1 to 1.5:1.

The aminoethylation reaction will generally be carried out over a period of about 2 to 24 hours, and preferably over a period of about 3 to 20 hours. Upon completion of the reaction, the desired polyalkyphenoxyaminoalkane is isolated using conventional techniques.

EXAMPLES

The invention will be further illustrated by the following examples, which set forth particularly advantageous process embodiments. While the Examples are provided to illustrate the present invention, they are not intended to limit it. This application is intended to cover those various changes and substitutions that may be made by those skilled in the art without departing from the spirit and scope of the appended claims.

Table 1 summarizes the key variables covered in the examples while Table 2 summarizes the results.

TABLE 1

Summary of Key Variables in Examples 1–4

| Example No. (Test No.) | Condition of Starting 4-Polyisobutylphenol Solution* | Alcohol Co-solvent |
| --- | --- | --- |
| 1 (N1) | Unfiltered | 1-Hexanol |
| 2 (N4) | Filtered | 1-Hexanol |
| 3 (N6) | Unfiltered | None |
| 4 (N7) | Filtered | None |
| 5 (N8) | Unfiltered | Hexanol, Mixed isomer |

*Unfiltered solution contains sediment from neutralized $BF_3$ alkylation catalyst.

TABLE 2

Summary of Results in Examples 1–4

| Example No. | 1 | 2 | 3 | 4 | 5 |
| --- | --- | --- | --- | --- | --- |
| Alkylphenol Conversion, % | 74 | 75 | 51 | 62 | 80 |
| Selectivity to Aminoethylate, % | 88 | 91 | 66 | 87 | 94 |
| Filtrate Properties | | | | | |
| Polymer Content, % | 70.4 | 73.9 | 77.8 | 73.8 | 67.4 |
| Aminoethylate Content, % | 42 | 47 | 26 | 39 | 47 |
| Basic N, % | 0.664 | 0.748 | 0.388 | 0.573 | 0.677 |
| Total N, % | 0.815 | 0.902 | 0.646 | 0.770 | 0.901 |
| Ethanolamine, % | <0.01 | 0.08 | <0.01 | <0.01 | <0.01 |
| Color, D1500 | 6.0 | 2.5 | 6.0 D* | 7.5 | 3.5 |

*Diluted 15 volumes of sample to 85 volumes of solvent.

Example 1

Preparation of Solution Containing

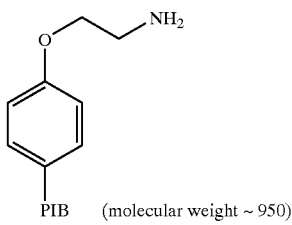

(molecular weight ~ 950)

Potassium hydroxide (assay 85%, 17.3 grams) and a solution of 4-polyisobutyl phenol wherein the polyisobutyl group has an average molecular weight of about 950 (2521.3 grams, prepared as in Example 1 of U.S. Pat. No. 5,300,701 except it was unwashed to remove the salts from the neutralized alkylation catalyst) were added to a 4-L reaction flask equipped with a magnetic stirrer, Dean-Stark trap, reflux condensor, nitrogen inlet and temperature controller. The solution of 4-polyisobutyl phenol contained about 32.7% Solvesso 100 aromatic solvent and had a hydroxyl number of 38.8 mg KOH/g. The solution also contained 5.3% unconverted polyisobutylene on a solvent-free basis. The reaction mixture was heated at about 130° C. under a pressure of about 150–160 mm Hg until no more water came overhead by azeotropic distillation with the aromatic solvent. The reactor contents were cooled under nitrogen and the solution of dehydrated 4-polyisobutyl phenol (2410.6 grams) was transferred to jars and stored in a dry box until needed for the aminoethylation reaction.

Dehydrated 4-polyisobutyl phenol solution (400.0 grams) from above, 1-hexanol (29.2 grams, anhydrous), ethanolamine (17.6 grams, redistilled), and diethyl carbonate (34.1 grams, anhydrous) were added to a separate 1-L reactor equipped with a fractionation column, a condenser and a receiver. The 36.5-cm×3-cm ID column was packed to a height of 28.5 cm with 4-mm, 316 stainless steel protruded packing (Pro-Pak®, part number L-3947-A20 from Cannon Instrument Company, State College, Pa.). The reaction mixture was heated slowly to about 150° C. under a pressure of about 650 mm Hg in order to distill off ethanol. The packed column helped keep diethylcarbonate and solvents in the reactor by natural reflux. The overhead distillate (25.5 grams) contained 88.8% ethanol and 1.1% diethyl carbonate. The column was removed and the reactor was set up for total reflux operation. The temperature was increased to about 178° C. and the pressure was adjusted to about 750 mm Hg in order to cause a vigorous reflux. These reaction conditions were maintained for four hours.

The reactor was cooled to about 85° C. Magnesium silicate (11.7 grams Magnesol HMR LS), filter aid (1.17 grams of Celite HyFlo Super Cel), and deionized water (2.21 grams) were added to the crude product and the mixture stirred for one hour at about 85° C. The crude product mixture was filtered with a pressure filter and yielded 362.7 grams of amber colored filtrate and 29.7 grams of filter cake. Table 2 summarizes the properties of the filtrate.

After evaporating solvent from the filtrate in a vacuum oven at about 150° C., $^1$H NMR (CDCl$_3$) was used to quantify the conversion of 4-polyisobutyl phenol and the selectivity to aminoethylate. Unconverted 4-polyisobutyl gives a doublet at 6.73 ppm for two protons on the aromatic ring, while converted 4-polyisobutyl gives a doublet at 6.81 ppm for the same two protons. The aminoethylate was identified by 7.25 (ABq, 2H), 6.8 (ABq, 2H), 4.0 (t, 2H), 3.1 (t, 2H) as described in the examples of U.S. Pat. No. 6,384,280, and the mole percent aminoethylate was calculated based on the NMR data. The aminoethylate content was converted to a weight percent solvent-free sample basis by combining the NMR data (mole percent) with the percent residual polyisobutylene content and component molecular weights calculated from the hydroxyl number of the 4-polyisobutyl phenol. This result was multiplied by the fraction of nonvolatile residue (polymer content) to obtain the weight percent aminoethylate on as-is sample. The estimated yield of aminoethylate in the filtrate was 153 grams based on the determined weight percent. The conversion of polyisobutylphenol was 74% and the selectivity to aminoethylate was 88% (Table 2).

The total nitrogen is higher than the basic nitrogen because the product contains some byproducts. These include acylated intermediate that has not yet rearranged to form the aminoethylate, a urea byproduct from further reaction of the aminoethylate, and possibly traces of other nitrogen-containing impurities.

Example 2

Preparation of Solution Containing

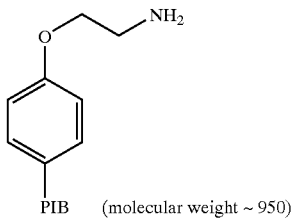

PIB   (molecular weight ~ 950)

Potassium hydroxide (assay 85%, 12.3 grams) and a solution of 4-polyisobutyl phenol wherein the polyisobutyl group has an average molecular weight of about 950 (2523.5 grams, prepared as in Example 1 of U.S. Pat. No. 5,300,701) were added to a 4-L reaction flask equipped with a magnetic stirrer, Dean-Stark trap, reflux condenser, nitrogen inlet and temperature controller. The solution of 4-polyisobutyl phenol contained about 26.1% Total Solvarex 9 aromatic solvent and had a hydroxyl number of 41.4 mg KOH/g. There was no sediment from the neutralized alkylation catalyst in this solution. The solution also contained 4.8% unconverted polyisobutylene on a solvent-free basis. The reaction mixture was heated at about 130° C. under a pressure of about 130–140 mm Hg until no more water came overhead by azeotropic distillation with the aromatic solvent. The reactor contents were cooled under nitrogen and the solution of dehydrated 4-polyisobutyl phenol (2406.1 grams) was transferred to jars and stored in a dry box until needed for the aminoethylation reaction.

Dehydrated 4-polyisobutyl phenol solution (400.0 grams) from above, 1-hexanol (31.2 grams, anhydrous), ethanolamine (18.9 grams, redistilled), and diethyl carbonate (36.5 grams, anhydrous) were added to a separate 1-L reactor equipped with a fractionation column, a condenser and a receiver. The reaction mixture was heated slowly to about 160° C. under a pressure of about 700 mm Hg in order to distill off ethanol. The overhead distillate (27.3 grams) contained 87.4% ethanol and 6.4% diethyl carbonate. The column was removed and the reactor was set up for total reflux operation. The temperature was increased to about 176° C. under atmospheric pressure to create a vigorous reflux. Since the pressure was not lowered, a nitrogen flow was maintained to the head of the reactor in order to carry away the $CO_2$ as it was generated by the reaction. These reaction conditions were maintained for four hours.

The reactor was cooled to about 75° C. Magnesium silicate (8.35 grams Magnesol HMR LS), filter aid (0.84 grams of Celite HyFlo Super Cel), and deionized water (1.57 grams) were added to the crude product and the mixture stirred for one hour at about 75° C. The crude product mixture was filtered with a pressure filter and yielded 384.8 grams of filtrate and 25.5 grams of filter cake. Table 2 summarizes the properties of the filtrate.

The estimated yield of aminoethylate in the filtrate was 180 grams. Conversion and selectivity (Table 2) were slightly better than in Example 1 because the starting solution of 4-polyisobutyl phenol did not contain sediment from the neutralized $BF_3$ alkylation catalyst. The basic nitrogen and total nitrogen contents of the Example 2 filtrate were slightly higher than in Example 1, reflecting the differences in conversion and selectivity. Color of the filtrate solution was also much lighter compared to Example 1. In this example 0.10 equivalents of KOH were used per equivalent of 4-polyisobutyl phenol, while in Example 1 we used 0.15 equivalents to compensate for any loss due to reaction of the KOH with the sediment in the 4-polyisobutyl phenol solution.

Example 3

Preparation of Solution Containing

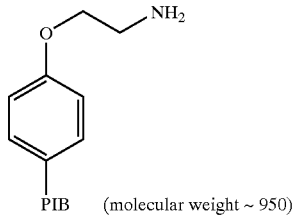

PIB   (molecular weight ~ 950)

Dehydrated 4-polyisobutyl phenol solution like prepared in Example 1 (400.0 grams), ethanolamine (17.7 grams, redistilled), and diethyl carbonate (34.2 grams, anhydrous) were added to a separate 1-L reactor equipped with a fractionation column, a condenser and a receiver. No 1-hexanol co-solvent was used in this experiment. The reaction mixture was heated slowly to about 150° C. under a pressure of about 700 mm Hg in order to distill off ethanol. The overhead distillate (25.8 grams) contained 98.5% ethanol, 1.4% diethyl carbonate, and <0.01% ethanolamine. The column was removed and the reactor was set up for total reflux operation. The temperature was increased to about 180° C. and the pressure was adjusted to about 708 mm Hg in order to create a vigorous reflux. These reaction conditions were maintained for four hours.

The reactor was cooled to about 75° C. Magnesium silicate (11.7 grams Magnesol HMR LS), filter aid (1.17 grams of Celite HyFlo Super Cel), and deionized water (1.86 grams) were added to the crude product and the mixture stirred for one hour at about 75° C. The crude product mixture was filtered with a pressure filter and yielded 322.0 grams of filtrate and 34.8 grams of filter cake. Table 2 summarizes the properties of the filtrate.

The estimated yield of aminoethylate in the filtrate was 83 grams. Alkylphenol conversion and selectivity to aminoethylate were significantly lower compared to Examples 1 and 2 (Table 2). Basic nitrogen and total nitrogen contents of the Example 3 filtrate were lower than in the filtrates of Examples 1–2. Also, the filtrate in Example 3 was much darker in color than in Examples 1–2. This illustrates the benefit of using an alcohol co-solvent.

Example 4

Preparation of Solution Containing

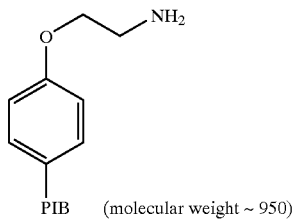

PIB   (molecular weight ~ 950)

Dehydrated 4-polyisobutyl phenol solution like prepared in Example 2 (400.0 grams), Exxon Aromatic 100 solvent (37.3 grams), ethanolamine (18.9 grams, redistilled), and diethyl carbonate (36.5 grams, anhydrous) were added to a separate 1-L reactor equipped with a fractionation column, a condenser and a receiver. No 1-hexanol co-solvent was used in this experiment. The reaction mixture was heated slowly to about 155° C. under a pressure of about 700 mm Hg in order to distill off ethanol. The overhead distillate (26.6 grams) contained 97.5% ethanol, 2.5% diethyl carbonate, and <0.01% ethanolamine. The column was removed and the reactor was set up for total reflux operation. The temperature was increased to about 180° C. and the pressure was adjusted to about 680 mm Hg in order to create a vigorous reflux. These reaction conditions were maintained for four hours:

The reactor was cooled to about 75° C. Magnesium silicate (8.35 grams Magnesol HMR LS), filter aid (0.84 grams of Celite HyFlo Super Cel), and deionized water (1.45 grams) were added to the crude product and the mixture stirred for one hour at about 75° C. The crude product mixture was filtered with a pressure filter and yielded 384.5 grams of filtrate and 23.2 grams of filter cake. Table 2 summarizes the properties of the filtrate.

The estimated yield of aminoethylate in the filtrate was 149 grams. The example again confirms the benefit to conversion and filtrate color of employing an alcohol co-solvent (Table 2).

Example 5

Preparation of Solution Containing

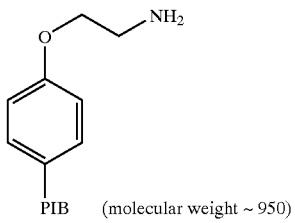

Dehydrated 4-polyisobutyl phenol solution like prepared in Example 1 (400.0 grams), mixed isomer hexanol (29.3 grams, Exxal 6 from ExxonMobil Chemical Company, dried by distillation), ethanolamine (17.5 grams, redistilled), and diethyl carbonate (34.2 grams, anhydrous) were added to a separate 1-L reactor equipped with a fractionation column, a condenser and a receiver. The reaction mixture was heated slowly to about 150° C. under a pressure of about 700 mm Hg in order to distill off ethanol. The overhead distillate yield was 24.4 grams. The column was removed and the reactor was set up for total reflux operation. The temperature was increased to about 174° C. under atmospheric pressure to create a vigorous reflux. Since the pressure was not lowered, a nitrogen flow was maintained to the head of the reactor in order to carry away the $CO_2$ as it was generated by the reaction. These reaction conditions were maintained for four hours.

The reactor was cooled to about 75° C. Magnesium silicate (11.7 grams Magnesol HMR LS), filter aid (1.17 grams of Celite HyFlo Super Cel), and deionized water (1.99 grams) were added to the crude product and the mixture stirred for one hour at about 75° C. The crude product mixture was filtered with a pressure filter and yielded 388.6 grams of filtrate and 28.8 grams of filter cake. Table 2 summarizes the properties of the filtrate.

The estimated yield of aminoethylate in the filtrate was 182 grams. This example gives results similar to Examples 1–2 and shows that a mixed-isomer hexanol co-solvent (about 62% branched-chain and about 38% straight-chain isomers by GC) works just as well as 1-hexanol. This example also confirms the benefit to conversion and filtrate color of employing an alcohol co-solvent.

What is claimed is:

1. A process for the preparation of a polyalkylphenoxyaminoalkane which comprises the aminoethylation of a polyalkylphenol compound in the presence of a basic catalyst with β-amino alcohol or a derivative thereof having the following formula:

$$R_1NH\text{—}CHR_2\text{—}CH_2\text{—}OH$$

wherein $R_1$, and $R_2$ are independently hydrogen or lower alkyl having 1 to about 6 carbon atoms, hydroxylalkylene, phenyl, alkaryl, or aralkyl,
and a dialkyl carbonate having the following formula $$(R_3O)_2CO$$

wherein $R_3$ is lower alkyl having 1 to about 6 carbon atoms; and wherein the polyalkyl group of said polyalkylphenol has an average molecular weight in the range of about 600 to 5,000.

2. The process according to claim 1, wherein the polyalkyl group has a molecular weight in the range of about 600 to 3,000.

3. The process according to claim 2, wherein the polyalkyl group has a molecular weight in the range of about 700 to 3,000.

4. The process according to claim 3, wherein the polyalkyl group has a molecular weight in the range of about 900 to 2,500.

5. The process according to claim 1, wherein the polyalkyl group is derived from polypropylene, polybutene, or a polyalphaolefin oligomer of 1-octene or 1-decene.

6. The process according to claim 5, wherein the polyalkyl group is derived from polyisobutene.

7. The process according to claim 6, wherein the polyisobutene contains at least about 20 wt % of a methylvinylidene isomer.

8. The process according to claim 1, wherein one of $R_1$ and $R_2$ is hydrogen or lower alkyl of 1 to about 4 carbon atoms, and the other is hydrogen; and $R_3$ is lower alkyl of 1 to about 4 carbon atoms.

9. The process according to claim 8, wherein one of $R_1$ and $R_2$ is hydrogen, methyl, or ethyl, and the other is hydrogen; and $R_3$ is methyl, ethyl, propyl, isopropyl, butyl or isobutyl.

10. The process according to claim 9, wherein $R_1$ is hydrogen, methyl, or ethyl, $R_2$ is hydrogen, and $R_3$ is methyl, ethyl, propyl, isopropyl, butyl or isobutyl.

11. The process according to claim 10, wherein both $R_1$ and $R_2$ are hydrogen and $R_3$ is methyl or ethyl.

12. The process according to claim 11, wherein both $R_1$ and $R_2$ are hydrogen and $R_3$ is ethyl.

13. The process according to claim 1, wherein the basic catalyst is selected from the group consisting of alkali metal lower alkoxide, alkali hydride or alkali metal hydroxide.

14. The process according to claim 13, wherein the alkali metal lower alkoxide is selected from the group consisting of sodium methoxide, potassium methoxide, sodium ethoxide, potassium ethoxide, sodium propoxide, potassium propoxide, sodium isopropoxide, potassium isopropoxide, sodium butoxide, potassium butoxide.

15. The process according to claim 14, wherein the alkali metal lower alkoxide is sodium methoxide.

16. The process according to claim 13, wherein the alkali hydride is sodium hydride or potassium hydride.

17. The process according to claim 13, wherein the alkali metal hydroxide is selected from the group consisting of sodium hydroxide, lithium hydroxide, or potassium hydroxide.

18. The process according to claim 17, wherein the alkali metal hydroxide is sodium hydroxide or potassium hydroxide.

19. The process according to claim 1, wherein the aminoethylation temperature is in the range of about 100° C. to 250° C.

20. The process according to claim 19, wherein the aminoethylation temperature is in the range of about 130° C. to 210° C.

21. The process according to claim 1, wherein the molar ratio of β-amino alcohol and dialkyl carbonate to polyalkylphenol is about 0.9–5:0.9–5:1.

22. The process according to claim 21, wherein the molar ratio of β-amino alcohol and dialkyl carbonate to polyalkylphenol is about 1–2:1–2:1.

23. The process according to claim 1, wherein the number of equivalents of basic catalyst per equivalent of polyalkylphenol is about 0.05:1 to 1:1.

24. The process according to claim 23, wherein the number of equivalents of basic catalyst per equivalent of polyalkylphenol is about 0.1:1 to 1:1.

25. The process according to claim 1, wherein the process is carried out in the presence of an alcohol co-solvent.

26. The process according to claim 1, wherein the alcohol co-solvent has the structure $R_4$—OH, wherein $R_4$ is an alkyl group having about 4 to 13 carbon atoms.

27. The process according to claim 26, wherein $R_4$ is an alkyl group having about 6 to 8 carbon atoms.

28. The process according to claim 27, wherein $R_4$ is an alkyl group having about 6 carbon atoms.

29. The process according to claim 28, wherein the alcohol co-solvent is hexanol, either branched, straight chain or mixtures thereof.

30. The process according to claim 1, wherein the molar ratio of alcohol co-solvent to polyisobutylphenol is about 0.2:1 to 5:1.

31. The process according to claim 30, wherein the molar ratio of alcohol co-solvent to polyisobutylphenol is about 0.4:1 to 2:1.

32. The process according to claim 31, wherein the molar ratio of alcohol co-solvent to polyisobutylphenol is about 0.5:1 to 1.5:1.

* * * * *